US010740719B2

(12) United States Patent
Kaweske et al.

(10) Patent No.: US 10,740,719 B2
(45) Date of Patent: Aug. 11, 2020

(54) METHODS, SYSTEMS, APPARATUSES AND DEVICES FOR FACILITATING PROVISIONING OF AN AUDIT DATA CORRESPONDING TO A BIOLOGICAL TARGET MATTER

(71) Applicant: JW Colorado LLC, Colorado Springs, CO (US)

(72) Inventors: John Kaweske, Colorado Springs, CO (US); Danielle Camargo, Colorado Springs, CO (US)

(73) Assignee: JW COLORADO LLC, Colorado Springs, CO (US)

(*) Notice: Subject to any disclaimer, the term of this patent is extended or adjusted under 35 U.S.C. 154(b) by 0 days.

(21) Appl. No.: 16/368,286

(22) Filed: Mar. 28, 2019

(65) Prior Publication Data

US 2019/0303846 A1  Oct. 3, 2019

Related U.S. Application Data

(60) Provisional application No. 62/649,268, filed on Mar. 28, 2018, provisional application No. 62/651,572, filed on Apr. 2, 2018.

(51) Int. Cl.
*G06Q 10/08* (2012.01)
*G16H 20/10* (2018.01)

(52) U.S. Cl.
CPC ....... *G06Q 10/087* (2013.01); *G06Q 10/0832* (2013.01); *G16H 20/10* (2018.01)

(58) Field of Classification Search
CPC ... G06Q 10/087; G06Q 10/0832; G16H 20/10
USPC ....................................... 340/572.1
See application file for complete search history.

(56) References Cited

U.S. PATENT DOCUMENTS

| | | | |
|---|---|---|---|
| 2014/0099614 A1* | 4/2014 | Hu | G09B 19/00 434/236 |
| 2017/0024689 A1* | 1/2017 | Dufour | G06Q 10/08 |
| 2017/0199168 A1* | 7/2017 | Jackson, Jr. | G01N 33/0098 |
| 2017/0266397 A1* | 9/2017 | Mayle | A61M 11/042 |
| 2018/0004682 A1* | 1/2018 | Kovach | H04L 9/3242 |
| 2018/0060518 A1* | 3/2018 | Pappas | G06F 19/00 |
| 2018/0280637 A1* | 10/2018 | Mayle | A61M 15/0048 |
| 2018/0326291 A1* | 11/2018 | Tran | A61B 5/0022 |
| 2019/0026716 A1* | 1/2019 | Anbukkarasu | G06Q 20/206 |
| 2019/0197544 A1* | 6/2019 | Frost | G06Q 30/0255 |

* cited by examiner

*Primary Examiner* — Hirdepal Singh

(57) ABSTRACT

Disclosed herein is a method of facilitating provisioning of an audit data corresponding to a biological target matter, in accordance with some embodiments. Accordingly, the method may include a step of receiving, using a communication device a monitoring data and a tracker data associated with the biological target matter from at least one of a plurality of end-point devices. Further, the method may include a step of creating, using a processing device, the audit data associated with the biological target matter based on at least one of the monitoring data and the tracker data. Further, the method may include a step of storing, using a distributed storage device, the audit data using block-chain technology.

18 Claims, 11 Drawing Sheets

METHODS, SYSTEMS, APPARATUSES AND DEVICES FOR FACILITATING PROVISIONING OF AN AUDIT DATA CORRESPONDING TO A BIOLOGICAL TARGET MATTER

The current application claims a priority to the U.S. Provisional Patent application Ser. No. 62/649,268 filed on Mar. 28, 2018 and a priority to the U.S. Provisional Patent application Ser. No. 62/651,572 filed on Apr. 2, 2018.

TECHNICAL FIELD

Generally, the present disclosure relates to the field of data processing. More specifically, the present disclosure relates to methods, systems, apparatuses and devices for facilitating provisioning of an audit data corresponding to a biological target matter.

BACKGROUND

Generally, patients take medicines that may be provided to them by hospitals or medical stores. Further, there may be no possible way to verify the authenticity of the medicine. Furthermore, there may be a possibility where the original medicine may be swapped by a fake one.

Further, usage of some biological target matter such as cannabis is still illegal federally, but still, in many states medicinal cannabis, which may be provided to patients as per doctor's recommendations, is legal. However, the uncertainty of possession of cannabis from an illegal source is always present. A proper way to determine the provenance of the biological target matter is not present. There is no single system to determine the provenance of the biological target matter to the consumer as well as to law enforcement.

Therefore, there is a need for improved methods, systems, apparatuses and devices for facilitating provisioning of an audit data corresponding to a biological target matter that may overcome one or more of the above-mentioned problems and/or limitations.

BRIEF SUMMARY

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is a method of facilitating provisioning of an audit data corresponding to a biological target matter, in accordance with some embodiments. Accordingly, the method may include a step of receiving, using a communication device a monitoring data and a tracker data associated with the biological target matter from at least one of a plurality of end-point devices. Further, the method may include a step of creating, using a processing device, the audit data associated with the biological target matter based on at least one of the monitoring data and the tracker data. Further, the method may include a step of storing, using a distributed storage device, the audit data using block-chain technology.

Further disclosed herein is a system for facilitating provisioning of an audit data corresponding to a biological target matter, in accordance with some embodiments. Accordingly, the system may include a communication device configured for receiving a monitoring data and a tracker data associated with the biological target matter from at least one of a plurality of end-point devices. Further, the system may include a processing device configured for creating the audit data associated with the biological target matter based on at least one of the monitoring data and the tracker data. Further, the system may include a distributed storage device configured for storing the audit data using block-chain technology.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION

Figure 1:
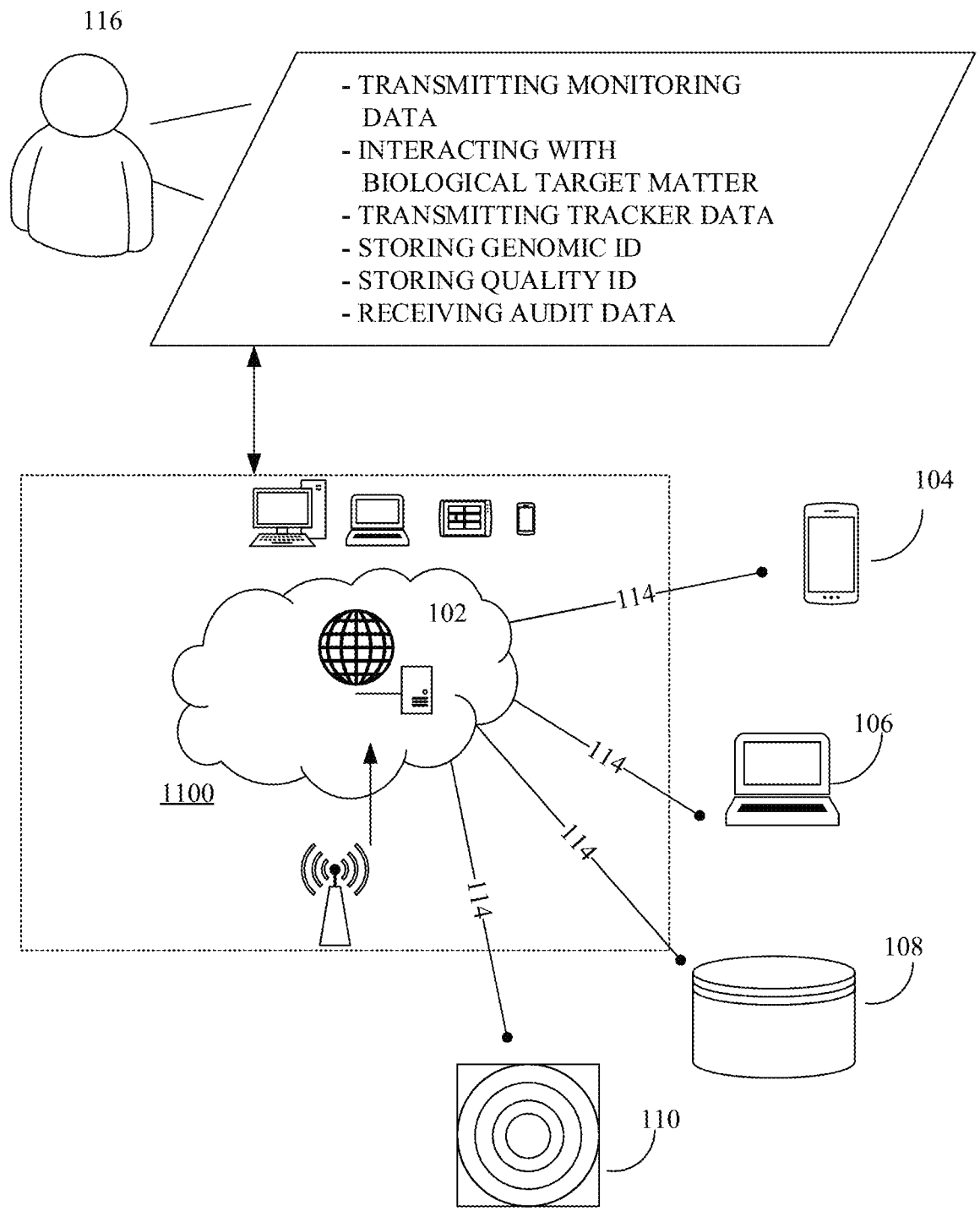
FIG. 1 is an illustration of an online platform consistent with various embodiments of the present disclosure

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of provisioning of an audit data corresponding to a biological target matter, embodiments of the present disclosure are not limited to use only in this context.

Overview

Auditable AI based multi-block-chain algorithmic approach deployed with IoT/IoNT (Internet of Things, Internet of Nano Things) system and methods for certifying, quantifying and qualifying, identifying, logging, tracking genomic traits at the macro and nano-scale of target matter; transportation certification from creation to retail and storage to distribution to consumer ownership; to provide macro and micro auditability from seed to sale, farm to fork, grain to glass or any other related supply-chain workflow.

The purpose of this invention is to provide a system of multi-algorithmic block-chain end to end solution to uniquely determine origin and destination of any target matter, for example, in the use case of legal cannabis, using IoT/IoNT, a unique multi-block-chain algorithmic approach as well as Artificial Intelligence.

Tracking target matter like plants (at the genomic and nano-levels), matter derivatives and other types of organic matter from seed to sale and/or farm to fork; uniquely using their genomic/genotype identification, internet of things and internet of nano-things as the base for a multi-block-chain protocol for genetic and quality certification; tracking, transport authentication/authorization, transfer to storage and retail, transfer to consumer; and auditing capabilities of such target matter (organic and even inorganic).

The disclosure proposes the creation of a new algorithm that utilizes a unique combination of algorithms for each phase of tracking from genome identification, to batch quality, to transport, to storage, to distribution, to sale and post-sale; as it could be used for auditing and validating origin, tracking transport, distribution, and sale to consumer. In post-sale, the disclosure would serve as a method to validate the authenticity of such target matter, allowing auditing capabilities to be exercised based on previous block-chain operations as well as available sensor data.

This multi-block-chain algorithmic approach, powered by AI, IoT, and IoNT, may be cloud based to serve from agriculture to supply-chain and logistics, to healthcare and other domains.

Challenge: To distinguish if a target matter, such as a cannabis plant for example, is from authentic and legal sources or not; or if a consumer is buying a plant the consumer believes it is; or, in this use case, if an illegal plant is sold as legal or if the legal plant is going to illegal hands. According to some embodiments, a single pane of glass system for tracking of biological target matter from genomic/nano-levels, to the transportation, to storage, consumer, to enforcement of auditing using block-chain based technology properly is disclosed.

Further, in some embodiments, the one or more block-chain algorithms may be used for the tracking and auditing of biological target matter.

Further, in some embodiments, the disclosure combines an AI powered multi-protocol algorithmic approach to fit full life cycle tracking at both the genomic and nano-levels, using IoT and Internet of Nano Things (IoNT) and several block-chains algorithms fit the purpose of each phase in the workflow.

Further, in some embodiments, the disclosure uses an AI-based multi-authenticator tied to IoT based and wearable solutions, IoT enabled smart cars and other IoT things that are part of a workflow; in the full context of this embodiment;

Further, in some embodiments, the disclosure leverages multi algorithmic block-chain and nano-sensors; in the full context of this embodiment;

Further, in some embodiments, the disclosure leverages combined AI (NLP, Deep Learning, Machine Learning); as in the full context of this embodiment.

High Level:

1—A multi algorithmic block-chain for capturing attributes for genetic, quality certification, IoT tracking through IoT chip/tagging at the macro but also at the nano-level using IoNT:

1.1 Proof of Existence Block-chain—AI monitored genomic sequencing, testing and modeling to map and log the genomic structure of the plant and create a genetic certification for this plant or target matter: (Proof of Existence is logged to block-chain). For example, in the use case of legal cannabis, all strains would be tested for genetics and have a genome sequenced. A unique key is generated that is to be logged onto the block-chain matching a unique QR code that is generated based on that end key. That unique key could be a mixture and in combination with a batch number and or producer's license number (or any other chosen attribute) is used to track this item back to its existence and provide linkage to the following algorithms:

1.2 Proof of Quality Block-chain—Batch testing and certification of percentages of elemental potency in the plant or target matter (for example, in the cannabis plant, the percentage and amount levels of THC, THCA, CBD, CBDN etc.): (Proof of Quality is logged to block-chain). A unique key is generated based on the combination of the Proof of Existence ID+Batch+License number (or a combination of chosen variables and/or attributes). Because batch numbers are different, even the same type of plant would have a unique ID based on the batch and license number and/or IoT tag tagged to the asset. Any other combination of attributes can be used to further qualify this plant and logged to the block-chain.

1.3 Proof of Space/Time—A block-chain and IoT/IoNT system to track the target matter from growing, to transportation, to the final destination and turn over to retail. Container carrying the target matter embedded with IoT capabilities (Proof of Space/Time) is used to track transportation: Proof of Space/Time is logged to the block-chain. A combination of authenticating and authorizing mechanisms may be combined to accept an authorization request for transportation and provide full traceability, security, and auditability to the transportation process. Vehicle (self-driven or man driven) or even vehicle to vehicle (V2V) communication may be enabled with the IoT sensor/chip to be authenticated and authorized with as part of the IoT transportation workflow lifecycle. For example, a combination of an IoT enabled ring with, for example, an NFC antenna used by the authorized carrier; a wearable vest with IoT enabled chip like NFC based; the IoT chip/sensor in a car along with the IoT chip/sensor in the carrying or transporting container will all communicate with each other to authorize, authenticate and track and log transport events to a plurality of end point devices.

At the end of the transportation process, a log to the block-chain will provide the Proof of Space/Time and the proper turn over to the storage and/or retail facility.

1.4 A block-chain and IoT/IoNT system to track from transportation to storage and/or retail, tracking the container with IoT tags. The carrier would have IoT/NFC or similar tags (i.e. embedded as a wearable NFC enabled carrier ring or with the tags embedded in a carrier vest) to allow the tracking and monitoring the transport. The carrying containers may also be enabled with IoT for traceability and interconnection with the Internet of Things part of this workflow.

1.4.1 A block-chain and IoT/IoNT system to track the transition of the transportation to the turn over to the retail or final destination for storage of the target matter. That will invoke a Proof of Provenance were the retail storage needs to also be part of the authentication and turnover of the asset by being IoT enabled (door knobs, POS, inventory tracking system, jars, containers and anything that participates in the transaction life cycle; from seed to sale, farm to fork, grain to glass for example).

1.5 A nano-level tracker that is inserted in the stalk or some other parts of the plant for tracking it from seed to sale, farm to fork, gain to glass or any other supply-chain workflow.

1.5.1 A nano-level tracker inserted into smart label or packaging can serve a two-fold purpose: monitor the chemical or biological changes as well as serve to validate Proof of Existence and/or Proof of Provenance, Proof of Ownership and/or Proof of Auditability and Quality of the monitored asset.

Detailed Level:

1—Proof of Existence: The purpose of the proof of existence is to document the genetic asset strain along with an IoT tag namespace for that strain to be logged to a block-chain. A combination of a set of uniquely identifiable and traceable characteristics, all creating and logging to a block on the block-chain and logging the properties of existence:

Possible Input: Proof of Existence Smart Contract, Genomics Sequencing Test, Programmable IoT (and IoNT) tags.

Possible Output: Logging the genomic test transaction, the IoT tag, and a combination of other possible items such as sensorial, nano, plasmid trackers, synthetic as possible ways to tag the matter uniquely.

The transaction ID is uniquely logged to a block on the block-chain. A unique QR code (or another standard scanable code type) is generated based on the genomics and any combination of other attributes such as the grower's license id, for instance.

Tracking chips, networks and sensors: Nano-sensors/Trackers, Sensorial sensor Trackers, PlasmID Sensor/Trackers, other potentials.

The nano-tracker can be used to track authenticity but can also monitor spoilage or harmful contaminants during distribution or storage which can be detected alongside enabled transfer of information regarding product conditions via nano-transmitters.

2—Proof of Quality: The purpose of Proof of Quality is to test, measure, qualify, quantify and document results of quality tests in regards to percentage of properties of a plant or target matter. Taking the input from Proof of Existence and adding another level of traceability: Proof of Quality: to measure properties on a plant. For instance, in the legal cannabis business, it would measure properties such as levels of THC, THCA, CBD, CBDA etc. levels in a plant. Additionally, prior to certifying via Proof of Quality, IoT tagging and sensors with artificial intelligence (NLP, ML, Deep Learning) may be combined to monitor the plants, growth, pH, water levels, soil moisture and pH, local temperature and humidity, CO2, etc. Such data could be used as annotation to Proof of Quality.

Possible Input: Proof of Quality Contract, Proof of Existence Transaction ID, target matter samples to be tested and logged to block-chain, other pertinent data points Possible Output: Proof of Quality is delivered in the form of the test results. The results are logged to the chip of the container that will hold the plant. The results are logged to the block-chain. The transaction ID is uniquely logged to a block on the block-chain. A unique QR code (or any other standardized scan-able code) is generated.

3—Proof of Space/Time: The purpose of the Proof of Space and Time is to track the target matter, for instance legal cannabis; from point A to B to ensure the transport is authorized, authenticated, monitored as well as intelligent and can't allow the target matter to be tampered with.

The tracking is at the nano, physical and geospatial levels using a combination of IoT sensors and actuators, IoNT through nano-trackers, and through other capabilities such as NFC and other chips for the macro world.

The communication can use a combination of cellular, wireless and satellite communication for the IoT connectivity to be supported. Nano-sensors, routers and actuators can use the terahertz band or another more nano-friendly band.

A Smart Transport contract which allows for the transport request and authorization of the target matter to be authenticated, tagged through several possible combinations of IoT enabled clothes, devices, wearables (such as NFC or other enabled rings, bracelets, badges and carrying containers as an example).

Possible Input: Proof of Space/Time Smart Contract, Proof of Existence and Proof of Quality Block-chain logs in order to request, allow, authenticate, authorize, multi-sign, track, monitor the end to end transport flow.

For example, an authorized person would require a series of combinations of IoT intelligent tags to allow for intelligent vehicles, cameras, other applications to be part of the ecosystem for tracking and authenticating the transport. Any authenticated driver would need to be facially recognized to be authorized besides being IoT enabled. In the case of self-driving vehicles or drones they would be enabled by IoT chips and be part of the transportation logistics by being pre scanned and authorized.

Possible Output: Logging the entire transport route, end to end and logging the transference to the retail, storage or final legal destination to the block-chain via tracked containers, vehicles and people. A unique QR code is generated.

4—Proof of Provenance: The purpose of the Proof of Provenance is to certify that the transported matter is of certified origin, quality, time/space through an authorized transport. It allows for the turn over from the transport to the storage and/or retail.

Possible Input: Proof of Existence+Proof of Quality+Proof of Space and Time

Possible Output: Logging Proof of Provenance for each delivered batch to the block-chain. A unique QR code is generated.

Nano-sensors could be applied in the design of the plants intelligent packaging. Sensors on the containers will allow them to be tracked. At a nanoscale, it can be used to identify Proof of Existence by scanning the nano-tracker and verifying if such batch contains a documented marker: silver nanoparticle or another documented trademark tracker, such as a plasmid.

At the macro level, for example, IoT chips such as NFC can be placed on the carrying container which intelligently communicates with sensors on the transporting vehicle; which in turns communicates with the carrier's badge or intelligence wearable IoT enabled vests, rings, bracelets, door knobs, etc. or anything IoT enabled that needs to be part of the transaction workflow.

5—Proof of Ownership: The purpose of Proof of Ownership is to allow the retail store to transfer the goods to the consumer in a traceable way which traces back to Proof of Existence to Quality to Space/Time. In the use case of legal cannabis for example, it is also to ensure only legal buyers are entitled to purchase and have their IoT enabled things to communicate with each other. A combination of intelligent tags on the pertinent items would allow for the transfer to the consumer to be tracked and logged as well.

For instance, a special ID card is tagged with IoT; the IoT enabled containers belonging to this user have to match that tagged ID card; participating thus in the sensing, communication and validation of the transaction. The retail sales as well as end user may have a smart application that reads the IoT tags and validates them via block-chain for this purchase and transfer of ownership.

Possible Input: Proof of Existence+Proof of Quality+Proof of Space and Time Possible Output: Authorized transfer to the consumer based on consumer's participation in the network. A unique QR code is generated and identifies the chain of assets in that purchase through the IoT capabilities of the entire ecosystem.

For example, if legal cannabis is found in a non-authorized container it can be deemed illegal. If a legal container has illegal or non-authentic target matter.

Sensors could be present on the user's containers, state or special id and smart application. IoT enabled containers are individually assigned to a legal user. For example, an IoT chip such as NFC and unique QR code or similar can be attached to the user's id; another could be attached to the medical containers belonging to the legal user. The container's IoT sensors communicate with the POS at the retailer, as well as with the user's IoT enabled ID. This would allow a synergy of IoT enabled devices (card, container, application) to intelligently communicate with each other to validate and authenticate the transaction.

6—Proof of Authority and Auditability: The purpose of the Proof of Authority is to allow an enforcer to audit the trail through the block-chain logs and positively identify if a matter has Proof of Existence, Quality, Space/Time, Provenance and Ownership.

It will allow to identify and certify if for example, in the case of legal cannabis, a plant is of legal precedence or not.

If the carrier has the Proof of Ownership by checking the audit trail and determining if the user has an authentic and or legal substance.

At the macro level, it can verify with a simple scan of the authorized code for the origin and block-chain traceability of this supply-chain.

At a nanoscale, it can be used to identify large quantities by scanning the nano-tracker and verifying if such batch contains a silver nanoparticle or another documented trademark tracker such as plasmid or any other.

Possible Input: Proof of Authority Contract, Proof of Ownership QR code or block-chain transaction ID. Tagged Container, with tagged user id and target matter.

Possible Output: The combination of the intelligent integration of the IoT tags on the user's container, user's ID, the POS system and other points of sensors and actuators will determine the Proof of Ownership; other triggers and events.

6.1—In the case of auditability through Proof of Authority, Proof of Ownership is determined via 2 ways:

1—A simple way is doing it at the macro level by scanning the Proof of Ownership code that is tagged to the container's label, for example, a QR code. This can be done with an application on a smart cell or tablet. It will pull all of the other blocks from the block-chains to show traceability back to Proof of Provenance, Proof of Space/Time, Proof of Quality and Proof of Existence.

2—The more intricate way that goes beyond visual inspection is the micro level. Let's say if the enforcer, such as for instance a state authority or another form of authority, apprehends a large number of plant matter in somebody's possession and wants to know if it came from a legal source; or from illegal sources. A test can be performed at the micro level. A nano-test to look at the nanoimprint done at the plant's unique identifier for instance or any other imprint that is a "nano-trademark" of that grower or provider. That would reveal if the plant has traceability to Proof of Existence, Quality, Space/Time; or if the plant matter is not authentic or legal.

Nano-Test Kit, similar to a Swimming Pool Test Kit, will test for the presence or absence of nanoparticles in the relevant sample via a simple colorimetric detection assay method. For example, if at the tracking level, plant were tagged with nano-particles of silver or gold or another taggable component not toxic to humans; at the nano-level;

the test would be able to detect if any sample belongs to a legal and traceable batch. By using both the block-chain traceability and the tagging at the macro level but also the micro, nano-level. Similarly, if the plant was tagged with a modified plasmid, it can also benefit from the method described above. Any nano or genomic imprint could be monitored and reported on via the nano-tracker using a target nanite using nano-sensors and nano-network to communicate and bridge data to the macro world.

Moreover, not only tracking the cannabis plant for instance, but also in terms of monitoring and reporting on the quality of the stored plant.

Nano-sensors could be utilized for example, in this use case, along the entire cannabis supply chain to detect different target events in sensitive, efficient and cost-effective ways. This nano-sensor is crucial in the process of monitoring and reporting on ensuring plant quality, safety, freshness, authenticity, and traceability via the "Proof of" block-chain algorithms. Based on the dynamic big data, a nanite could take actions based on events reported by the nano-sensor and the logic built to respond to event categories. For instance, in nano-IoT enabled package, it could sensor changes in freshness and report or alert based on predetermined actions.

AI

Artificial Intelligence can be used in this invention in innovative ways at many levels. On the configuration platform, AI based smart contract for the block-chain would be built by voice commands instead of programming Using NLP this would be a voice-operated platform for setting, configuring, administering and using the solution.

The second way is to use AI with IoT to detect new "things" to IoT without human intervention; via machine and deep learning. For example, in the case of a grow house, plants are monitored with IoT enabled tags (such as NFC for example) at the macro level; (and possibly with nano-trackers at the nano-level; or plasmid trackers at the genetic level); AI could be used to detect addition or removal of plants. For instance, if a new set of plants is added to a grow house, the AI platform would allow it to be picked up immediately and cataloged accordingly by processing IoT sensors in an adaptive mode.

AI could be used for growth and crop optimization: For an instance, AI could be used to monitor the soil or water during the growing phase of a plant, be the pivotal mechanism during transport (in combination with IoT) and as well as during distribution. This capability refers to the ability to combine technologies, such as IoT chips (i.e. NFC), with AI to provide several AI based capabilities: NLP for the conversational interface; ML and DL (Machine and Deep Learning) for the communication based on sensors and IoT communication with the AI framework. Besides, Machine and Deep Learning Modeling for the capabilities to set ideal values or thresholds for variables such as micro, macro nutrients, light cycle, water quality levels, $CO_2$ levels, soil quality levels, water and soil pH, energy efficiency, etc. may also be used. In this particular use case of legal cannabis for example, each monitoring, learning and tunable AI based processes may be tuned for each separate step in the grow life cycle: vegetative, pre-flowering, flowering etc. and for each type of plant family (i.e. *Sativa*, Indica etc.) and strain type. Deep Learning would be applied via AI analytics to the learning algorithms for each monitored plant cycle and provide optimization models as well as self-tuning based on both supervised and unsupervised learning models.

At the genomic level, AI could be used to detect any changes in the genomic structure of a monitored asset. Similarly, at the nano-level, nano-sensors enabled by AI could report changes to the physical, chemical and biological structure of the monitored asset. Machine and Deep Learning in AI could also be effectively used in this context. In the case of the genomic sequencing, AI machine learning could be used to monitor, predict or infer genetic variants. Any genome sequencing can be translated into a visual model. Any variation in the model could be picked up by AI deep learning.

This disclosure embodiment proposes to combine IoT enabled technologies such as NFC and other possibilities to the AI framework for requests, authorization, and authentication in many situations. For instance, tracking legal cannabis for end to end transportation logistics. This includes, NLP, voice, face recognition, multifactor AI based security authentication and authorization, integration to IoT (Internet of Things: chips, sensors, actuators etc.). The goal is to use NLP to authorize, authenticate, monitor and sign off on the full transportation logistics, in combination with IoT. NLP would be used in the voice recognition as well as providing a human like conversational interface to guide configuration, authorization workflows and any other tasks required in the transportation workflow. Machine and deep learning would be applied in face recognition of the authorized subject and in the dynamic interaction with IoT enabled things.

Algorithmic Workflows:

Producer Workflow (Certification: Proof of Existence [Genome sequencing, Testing and Logging] and Proof of Quality [Property and Potency Testing Per batch)—The Proof of Existence and Proof of Quality combine to generate a unique key which is logged to the Block-chain and is ready to authorize quality test and then transportation.

Transportation Workflow: (Multi-Signature: Proof of Existence key and Proof of Quality can authorize transportation.) A unique code is generated to allow registered transportation to transport from point A to B. Proof of Space and Time track and log all movements of assets through IoT. The transportation vehicle itself should be enabled with IoT capabilities to add another layer of authentication and verification. The carrier container (bag, bin or other) may also have an IoT tag and other biometric capabilities to allow carriers to be authenticated before tracking the asset in time and space. The carrier badge, clothes (or accessories like an IoT enabled ring, wristband, keychain etc.) could also contain an IoT tag that allows for the cross-reference of the carrier and the destination with the tracked asset, using IoT chips.

Storage Workflow: Proof of Provenance needs to be granted based on Proof of Space/Time, Proof of Quality and Proof of Existence.

Retail Workflow: Retail can be granted Proof of Ownership based on the previous workflow. Transfer from transport container to retail jars, in the case of legal cannabis, generates a new unique QR code for each jar in order to track and bind to previous workflows.

Consumer Workflow: Consumer needs to have an approved and tagged container which is bound to the user's id. Let's say for instance, in the case of legal cannabis. For medical or recreational cannabis, a tag such as NFC, could be attached to the user's ID as well as to the user's individually approved storage containers. The combination of these would allow the matter to be transferred to the user and sign off on Proof of Ownership.

Auditing Workflow: The auditing workflow has the macro and micro dimensions. For the macro, it would interact with an IoT (such as NFC) enabled device to read the tag of the container of such plant or target matter. It would allow for the enforcer to validate the supply-chain looking back at the Proof of Existence (genomic imprint) to Proof of Quality (Existence+Tested Batch with quality metrics) to Proof of Space/Time (IoT Enabled Transport tracking and hand shake;

IoNT possible to track containers) to Proof of Ownership (Retail, Consumer).

The enforcer would use the block-chain algorithms for Proof of Authority and Auditability to have the means to have access to the previous data points.

IoT Sensors that may be used in this invention:

IoT paradigm may be defined as a way to collect data from sensors (RFID, NFC, nano-transmitters, other types of sensors etc.) and to send control messages to actuators.

IoT Communication for this invention will be done at both the macro and micro:

1—IoT devices could be connected through satellites, across global borders to connect remote assets, logging each step to a block-chain. The vehicle or transportation used in the transport of the tracked matter would be communicating the route with the IoT/IoNT networks.

2—The IoNT devices would be connected through the IoNT network using the Terahertz band or another specific nano-band could also be integrated to communicate with the existing satellites, routers, cellular, wireless networks at the macro level. Nano-routers and macro routers could communicate through interconnecting bridges.

3—They can use nano-electromagnetic communications for Wireless Nano-sensor Networks (WNSNs). A nano-sensor could be seen as an integrated device around 10-100 µm2 in size that is capable of performing simple tasks.

Nano-sensors: Self-powered nano-sensors with a recognition mechanism through the DNA (Biomimetic, Enzymatic, Molecular recognition, antibody etc.) may be deployed as part of this solution.

The transducing mechanism can use a combination of optical absorption, fluorescence, polarization, luminescence etc.; mass (Acoustic wave, Microbalance, resonant etc.), electrochemical (Condumetric, Ion Sensitive Amperometric, Potentiometric etc.), or using piezoelectric, thermal or volatile gases and vapors ions. A combination of any sensor type and capability would allow for the tracking at the nano-level:

Physical nano-sensors: (that work on mass, pressure, force, displacement); Newly discovered nanomaterials such as graphene and its derivatives, like, Graphene Nanoribbons (GNRs) and carbon nanotubes may be used as the main materials for physical sensors. They work based on the fact that the electronic properties of both nanotubes and nanoribbons change when these are bent or deformed, making them a potential candidate for the implementation of these sensors.

Chemical nano-sensors: (that work on chemical composition, molecular concentration); these are used to measure magnitudes such as the concentration of a given gas, the presence of a specific type of molecules, or the molecular composition of a substance; physical sensors, when a nanotube or a nanoribbon is used in a transistor configuration, the presence of a specific type of molecules changes the on/off threshold voltage of the transistor.

Biological nano-sensors: (that work on DNA interaction, Enzymatic Interaction, Antibody interaction); these are used to monitor bio molecular processes such as antibody/antigen interactions, DNA interactions, enzymatic interactions or cellular communication processes, amongst others. A biological nano-sensor is usually composed of (i) a biological recognition system or bio receptor, such as an antibody, an enzyme, a protein or a DNA strain, and (ii) a transduction mechanism, e.g., an electrochemical detector, an optical transducer, or an amperometric, voltaic or magnetic detector.

This invention may be flexible to the two subtypes of biological nano-sensors that can be applied to this nano-tracking principle: electrochemical biological nano-sensors and photometric biological nano-sensors.

The electrochemical biological sensors operate in a similar way to chemical nano-sensors, but in this case, the change in the electronic properties of, for example, a CNT-based, FET transistor is induced either by:

(i) Any type of protein or any other chemical composite that binds itself to the functionalized nanotube. In this use case, for an instance, a form of terpenes (or any other chosen element) could be added to the cannabis plant, for instance, at the nano-level.

(ii) A particular antigen that binds itself to an antibody glued to the nanotube. In this case, the terpene (or any other chosen element) antigen could bind to the antibody of the target plant at the nano-level.

(iii) A single-stranded DNA chain that binds itself to another DNA chain which has been attached to the nanotube. In this case, a specific modification to the DNA could be attached to the nanotube. For instance, let's say in the use case of legal cannabis that each grow house is able to create a unique imprint on its plants, and several options can be used to implement it.

Additionally, specifically crafted nanites or nano-machines can be integrated to monitor and track location or changes in condition or another element. A nanite can be used on the DNA strain of a particular plant matter, for example, in the use case of legal cannabis.

A nano-sensor could trigger the nanite to perform an operation. This same nanite can be configured for different operations. It could be used to count the molecules inserted in nano-tube or present in a plat matter sample.

A nano-sensor could be triggered to check the nano-IoT tag in the target matter and publish an event based on the operation output. As an example, in the legal cannabis, an enforcer could take samples from a plant and run a scan using the nano-IoT tag to access the traceability of this matter on the block-chain. It would see if the plant is from a legitimate source or not. Tracing back via the block-chain and the IoT at the macro level, for instance, NFC tags on the cannabis containers; and at the micro level with the nanite and the IoNT combined capabilities to inspect and report of the authenticity of this plant or target matter.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor and at least one actuator. Examples of the one or more client devices and/or the server computer may include, a desktop computer, a laptop computer, a tablet computer, a personal digital assistant, a portable electronic device, a wearable computer, a smart phone, an Internet of Things (IoT) device, a smart electrical appliance, a video game console, a rack server, a super-computer, a mainframe computer, mini-computer, micro-computer, a storage server, an application server (e.g a mail server, a web server, a real-time communication server, an FTP server, a virtual server, a proxy server, a DNS server etc.), a quantum computer, and so on. Further, one or more client devices and/or the server computer may be configured for executing a software application such as, for example, but not limited to, an operating system (e.g. Windows, Mac OS, Unix, Linux, Android, etc.) in order to provide a user interface (e.g. GUI, touch-screen based interface, voice based interface, gesture based interface etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third party database, public database, a private database and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data finger-printing, role based access control, and so on.

Further, one or more steps of the method disclosed herein may be initiated, maintained, controlled and/or terminated based on a control input received from one or more devices operated by one or more users such as, for example, but not limited to, an end user, an admin, a service provider, a service consumer, an agent, a broker and a representative thereof. Further, the user as defined herein may refer to a human, an animal or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human readable secret data (e.g. username, password, passphrase, PIN, secret question, secret answer etc.) and/or possession of a machine readable secret data (e.g. encryption key, decryption key, bar codes, etc.) and/or or possession of one or more embodied characteristics unique to the user (e.g. biometric variables such as, but not limited to, fingerprint, palm-print, voice characteristics, behavioral characteristics, facial features, iris pattern, heart rate variability, evoked potentials, brain waves, and so on) and/or possession of a unique device (e.g. a device with a unique physical and/or chemical and/or biological characteristic, a hardware device with a unique serial number, a network device with a unique IP/MAC address, a telephone with a unique phone number, a smart-card with an authentication token stored thereupon, etc.). Accordingly, the one or more steps of the method may include communicating (e.g. transmitting and/or receiving) with one or more sensor devices and/or one or more actuators in order to perform authentication. For example, the one or more steps may include receiving, using the communication device, the secret human readable data from an input device such as, for example, a keyboard, a keypad, a touch-screen, a microphone, a camera and so on. Likewise, the one or more steps may include receiving, using the communication device, the one or more embodied characteristics from one or more biometric sensors.

Further, one or more steps of the method may be automatically initiated, maintained and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g. the server computer, a client device etc.) corresponding to the performance of the one or more steps, environmental variables (e.g. temperature, humidity, pressure, wind speed, lighting, sound, etc.) associated with a device corresponding to the performance of the one or more steps, physical state and/or physiological state and/or psychological state of the user, physical state (e.g. motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g. a real-time clock), a location sensor (e.g. a GPS receiver, a GLONASS receiver, an indoor location sensor etc.), a biometric sensor (e.g. a fingerprint sensor), an environmental variable sensor (e.g. temperature sensor, humidity sensor, pressure sensor, etc.) and a device state sensor (e.g. a power sensor, a voltage/current sensor, a switch-state sensor, a usage sensor, etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

FIG. 1 is an illustration of an online platform 100 consistent with various embodiments of the present disclosure. By way of non-limiting example, the online platform 100 to facilitate provisioning of an audit data corresponding to a biological target matter may be hosted on a centralized server 102, such as, for example, a cloud computing service. The centralized server 102 may communicate with other network entities, such as, for example, a mobile device 104 (such as a smartphone, a laptop, a tablet computer etc.), other electronic devices 106 (such as desktop computers, server computers etc.), databases 108, and sensors 110 over a communication network 114, such as, but not limited to, the Internet. Further, users of the online platform 100 may include relevant parties such as, but not limited to, end users, administrators, service providers, service consumers and so on. Accordingly, in some instances, electronic devices operated by the one or more relevant parties may be in communication with the platform.

A user 116, such as the one or more relevant parties, may access online platform 100 through a web based software application or browser. The web based software application may be embodied as, for example, but not be limited to, a website, a web application, a desktop application, and a mobile application compatible with a computing device 1100.

According to some embodiments, the online platform 100 may facilitate provisioning of an audit data corresponding to a biological target matter. The biological target matter may include a medicinal herb such as cannabis. Further, the audit data may be based on a data file and/or block-chain block on which data about the biological target matter such as plant type, genome sequencing, batch number etc., may be registered. The online platform 100 may communicate with at least one of Internet of Things (IoT) devices and Internet of Nano Things (IoNT) devices. Each device of the at least one of IoT devices and IoNT devices, such as an actuator, a sensor etc. may be uniquely identified through an embedded computing system. An IoT communication may be provided at both macro as well as micro level. On the macro level, IoT devices may connect to the online platform 100 through satellites, across global borders to connect remote devices and further may store each step to a block-chain. On a micro level, IoNT devices may be connected through an IoNT network using a Terahertz band or another specific nano-band that may also be integrated to communicate with the existing satellites, routers, cellular, wireless networks at the macro level. Nano-routers and macro-routers may communicate through an interconnecting bridge.

Further, in some embodiments, the IoT devices, as well as the IoNT devices, may be embedded into the biological target matter. Additionally, in some embodiments, Artificial Intelligence (AI) may also be utilized. AI integrated with IoT devices, IoNT devices, along with nano-sensors may facilitate in certifying, identifying, logging, and tracking genomic traits of a biological target matter at the macro as well as at a nanoscale. For an instance, a grow house where plants are cultivated may be monitored with IoT enabled tags (such as NFC) at the macro level, nano-trackers may be utilized at the micro level, and plasmid trackers may be utilized at a genetic scale. At the macro level, AI may be utilized to detect as well as identify increment or decrement in quantity of plants. For example, if a new set of plants are added to the grow house, the AI may recognize the addition of new plants immediately and accordingly store updated audit data on the block-chain. Similarly, at the micro level, changes to the physical, chemical and biological structure of the biological target matter may be observed, monitored and logged.

Further, AI smart contracts may be generated by a processing device such as a distributed app or computer. An AI smart contract may include a computer protocol that may be intended to digitally facilitate, verify, or enforce the negotiation or performance of a contract. The AI smart contracts for block-chain may be built by voice commands with the help of Natural Language Processing (NLP).

Further, the online platform 100 may receive each of monitoring information and tracker data from a plurality of intelligent packaging sensors. The intelligent packaging sensors may be installed on a packaging of the biological target matter. The intelligent packaging sensors may receive monitoring as well as tracker data from the biological target matter. Accordingly, the intelligent packaging sensors may transmit monitoring as well as tracker data to the online platform 100. A container may be used to transport the biological target matter which may be embedded with IoT tags that may store information. The container may contain a biometric sensor.

Further, a user identifier data associated with a user interacting with the biological target matter may be received by the online platform 100 through a communication device such as IoT, IoNT, and NFC etc. The user identifier data may include basic details related to the user such as name, age etc. Further, the user identifier data may comply with KYC (Know your Customer). Further, a time data associated with one or more of the location data and a user interaction may be received through the communication device. The location and time data that may be received by the online platform 100 may be helpful for the consumer as well as the merchant to track the biological target matter. For an instance, clothing or accessory embedded with IoT tags may be worn by the driver of the vehicle who may be transporting the biological target matter. Even IoT chips may be embedded in the vehicle. Accordingly, the online platform 100 may transmit the location and time data to the consumer when demanded.

Further, the audit data associated with the biological target matter based on the location data, the user identifier data and the time data may be generated using the processing device. For an instance, the online platform 100 may receive the location data, the user identifier data and the time data and accordingly the processing device may compute the audit data.

Further, the audit data using block-chain technology may be stored using a distributed storage device. The block-chain technology may provide a secure way to store data and may ensure that the data may not get tempered and lost.

Figure 2:
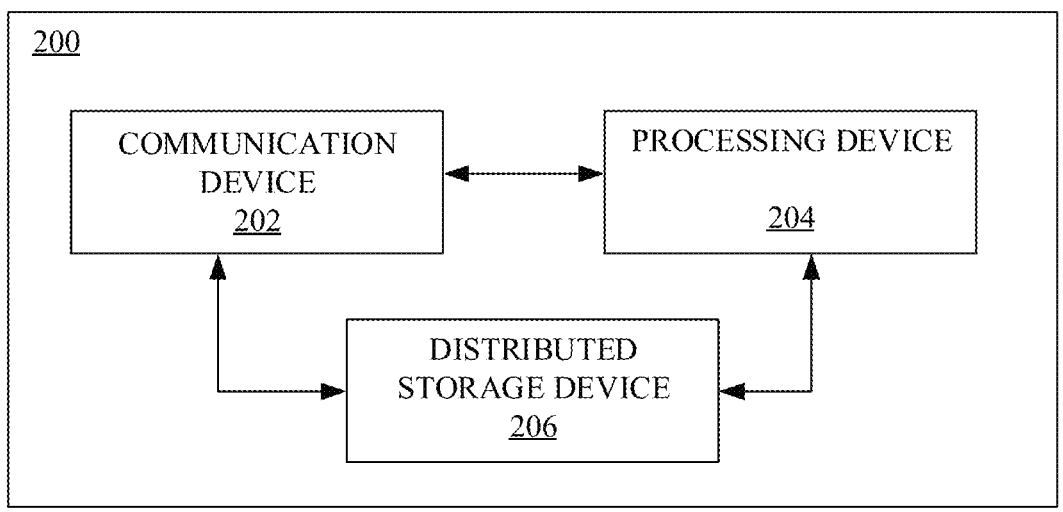
FIG. 2 is a system to facilitate provisioning of an audit data corresponding to a biological target matter, in accordance with some embodiments.

FIG. 2 is a system 200 to facilitate provisioning of an audit data corresponding to a biological target matter, in accordance with some embodiments. Further, the system 200 may comprise a communication device 202 configured for receiving a monitoring data and a tracker data associated with the biological target matter from at least one of a plurality of end-point devices. Further, the system 200 may include a processing device 204 configured for creating the audit data associated with the biological target matter based on at least one of the monitoring data and the tracker data. Further, the system 200 may include a distributed storage device 206 configured for storing the audit data using block-chain technology.

Further, in some embodiments, the communication device 202 may be configured for receiving a location data associated with the biological target matter. Further, the communication device 202 may be configured for receiving, a user identifier data associated with a user interacting with the biological target matter. Further, the communication device 202 may be configured for receiving a time data associated with one or more of the location data and the user interaction. Further, the processing device 204 may be configured for generating the audit data based on the location data, the user identifier data and the time data. Further, the location data associated with the biological target matter may be obtained from a location tracker associated with the biological target matter, such as a GPS tracker associated with the biological target matter.

Further, in some embodiments, the monitoring data may comprise at least one of a location data of the biological target matter, a user interaction data, and a time data associated with a user interaction. For instance, the monitoring data may include a time, and location of growing of the biological target matter. Further, the monitoring data may include data related to at least one step of a supply chain of the biological target matter. For instance, the monitoring data may include a proof of existence documenting a genetic asset of the biological target matter, as obtained through one or more tracking chips, nano-sensors and trackers. Further, the monitoring data may include a proof of quality documenting percentage of properties of the biological target matter, such as a genomic sequence, a DNA, a chemical composition, and so on, as obtained from chemical sensors measuring growth, pH, water levels, soil moisture and pH and so on. Further, the monitoring data may include a proof of space/time to track a movement of the biological target matter to ensure that the transport of the biological target matter may be authorized, authenticated, and monitored to prevent tampering, as obtained through one or more nano-trackers, location trackers, NFC chips, and so on transmitting recorded sensory data over a communication network such as a cellular network, wireless network, and so on. Further, the monitoring data may include a proof of provenance certifying that the biological target matter may be authentic as transported from an origin point, as authenticated from the hone or more nano-trackers, location trackers, NFC chips, and so on. Further, the monitoring data may include a proof of ownership to allow a retail store to transfer the biological target matter to a customer in a traceable manner. For instance, in the use case of legal cannabis, the proof of ownership may ensure that only legally allowed customers may be entitled to purchase the biological target matter.

Further, in some embodiments, the monitoring data may comprise chemical composition of the biological target matter. For instance, if the biological target matter includes legal cannabis strain, the monitoring data may comprise a chemical composition of the biological target matter including percentages of THC, CBD, and CBN in the legal cannabis.

Further, in some embodiments, the tracker data may comprise at least one of a value of a biological parameter associated with the biological target matter, and sensor data received from a packaging sensor associated with the packaging of the biological target matter. For instance, a biological parameter may include a DNA data, or genome sequence of the biological target matter, which may be obtained from a DNA marker embedded in the biological target matter at a time of growing. Further, the value of the biological parameter associated with the biological target matter may be inspected for consistency, wherein the value of the biological parameter, such as DNA, or the genome sequence may remain constant throughout a supply chain of the biological target matter from growth, to a final retail to an end consumer.

Further, in some embodiments, the packaging sensor may comprise at least one of an RFID tag, an NFC chip, an Internet of Things (IoT) tag and a nano-transmitter.

Further, in some embodiments, the audit data may be stored on an IoT tag associated with the biological target matter.

Further, in some embodiments, the processing device 204 may be further configured to use artificial intelligence to perform at least one of monitor at least one of a soil or a water during the growing phase of a plant, wherein the biological target matter may be obtained from the plant, detect changes in the genomic structure of a monitored plant, track the biological target matter during transportation and distribution, generating smart contracts, and providing analytics data related to the growing, transportation, and distribution of the biological parameter.

Further, in some embodiments, the processing device 204 may be configured to use Natural Language Processing (NLP) to generate smart contracts based on voice commands of a user.

Further, in some embodiments, the communication device 202 may be configured for receiving a tracker data from an end-point device. Further, the communication device 202 may be configured for transmitting, an audit data to the end-point device. Further, the distributed storage device 206 may be configured for retrieving the audit data based on the tracker data. Further, the audit data may include the monitoring data, and the tracker data. Further, the audit data may be used by a user, such as the customer to confirm that the biological target matter may be authentic.

Figure 3:
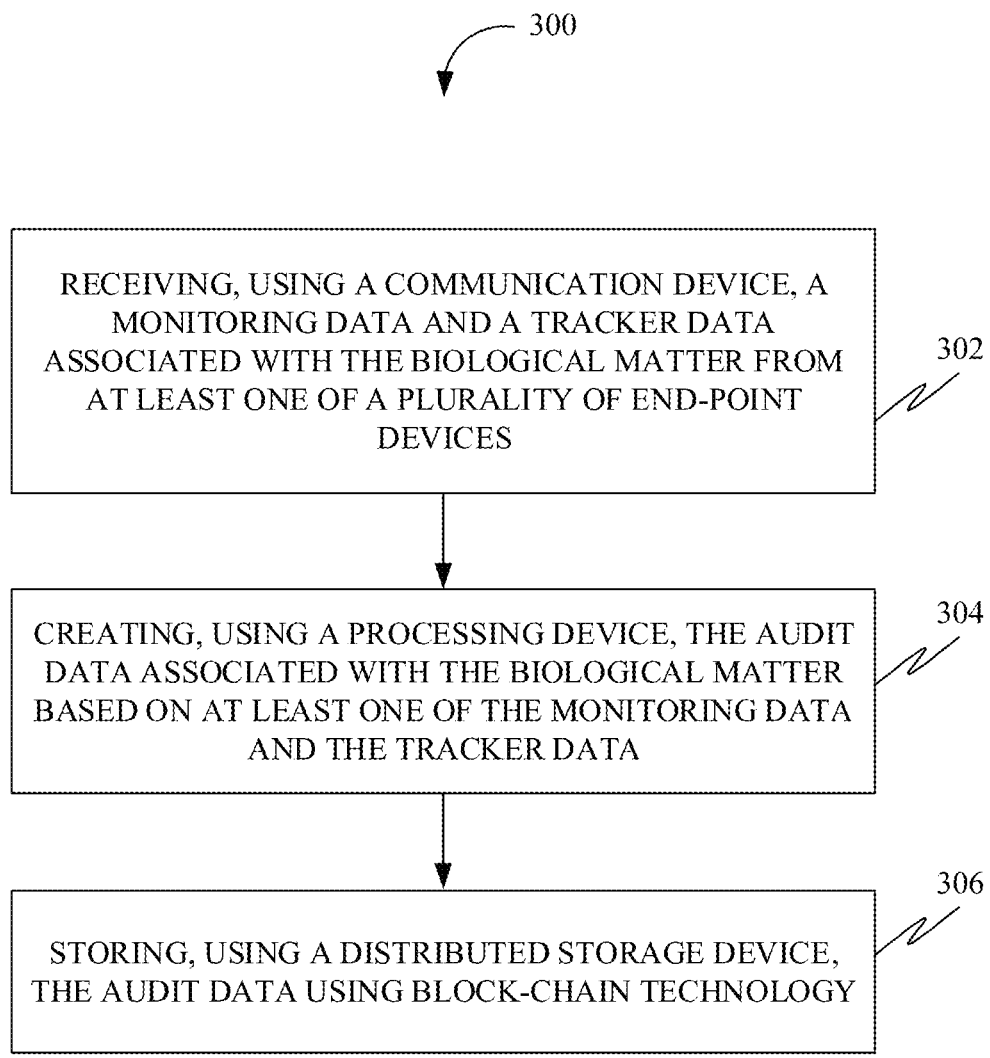
FIG. 3 is a flowchart of a method to facilitate provisioning of an audit data corresponding to a biological target matter, in accordance with some embodiments.

FIG. 3 is a flowchart of a method 300 to facilitate provisioning of an audit data corresponding to a biological target matter, in accordance with some embodiments. Further, at 302, the method 300 may include receiving, using a communication device, such as the communication device 202, a monitoring data and a tracker data associated with the biological target matter from at least one of a plurality of end-point devices.

Further, at 304, the method 300 may include creating, using a processing device, such as the processing device 204, the audit data associated with the biological target matter based on at least one of the monitoring data and the tracker data.

Further, at 306, the method 300 may include storing, using a distributed storage device, such as the distributed storage device 206, the audit data using block-chain technology.

Further, in some embodiments, the monitoring data may comprise at least one of a location data of the biological target matter, a user interaction data, and a time data associated with a user interaction.

Further, in some embodiments, the monitoring data may comprise chemical composition of the biological target matter.

Further, in some embodiments, the tracker data may comprise at least one of a value of a biological parameter associated with the biological target matter, and sensor data received from a packaging sensor associated with the packaging of the biological target matter.

Further, in some embodiments, the packaging sensor may comprise at least one of an RFID tag, an NFC chip, an Internet of Things (IoT) tag and a nano-transmitter.

Further, in some embodiments, the audit data may be stored on an IoT tag associated with the biological target matter.

Further, in some embodiments, the processing device may be configured to use artificial intelligence to monitor at least one of a soil or a water during the growing phase of a plant, wherein the biological target matter may be obtained from the plant. Further, the processing device may be configured to use artificial intelligence to detect changes in the genomic structure of a monitored plant. Further, the processing device may be configured to use artificial intelligence to track the biological target matter during transportation and distribution. Further, the processing device may be configured to use artificial intelligence for generating smart contracts. Further, the processing device may be configured to use artificial intelligence for providing analytics data related to the growing, transportation, and distribution of the biological parameter.

Further, in some embodiments, wherein the processing device may be further configured to use Natural Language Processing (NLP) to generate smart contracts based on voice commands of a user.

Figure 4:
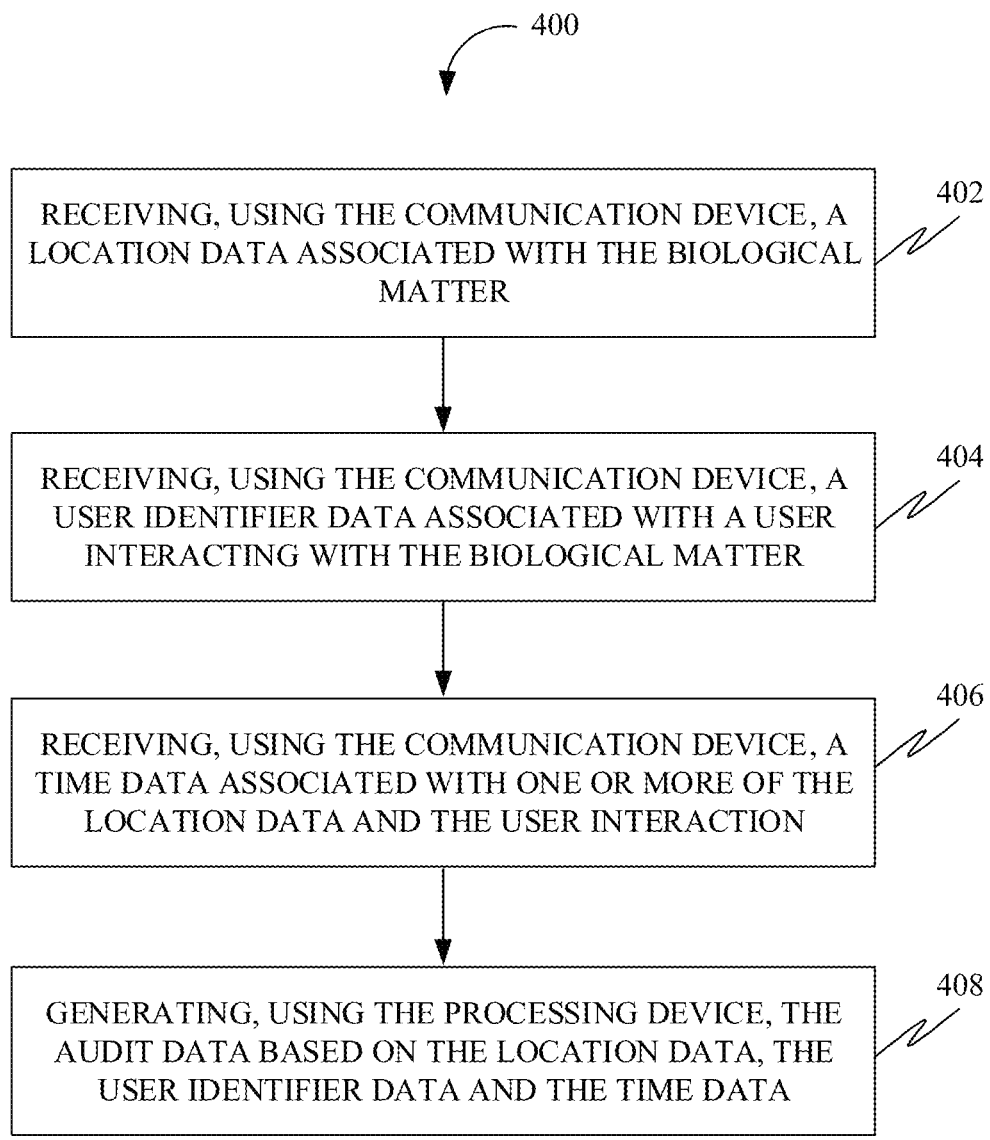
FIG. 4 is a flowchart of a method of creating the audit data, in accordance with some embodiments.

FIG. 4 is a flowchart of a method 400 of creating the audit data, in accordance with some embodiments. Further, at 402, the method 400 may include receiving, using the communication device, a location data associated with the biological target matter.

Further, at 404, the method 400 may include receiving, using the communication device, a user identifier data associated with a user interacting with the biological target matter.

Further, at 406, the method 400 may include receiving, using the communication device, a time data associated with one or more of the location data and the user interaction.

Figure 5:
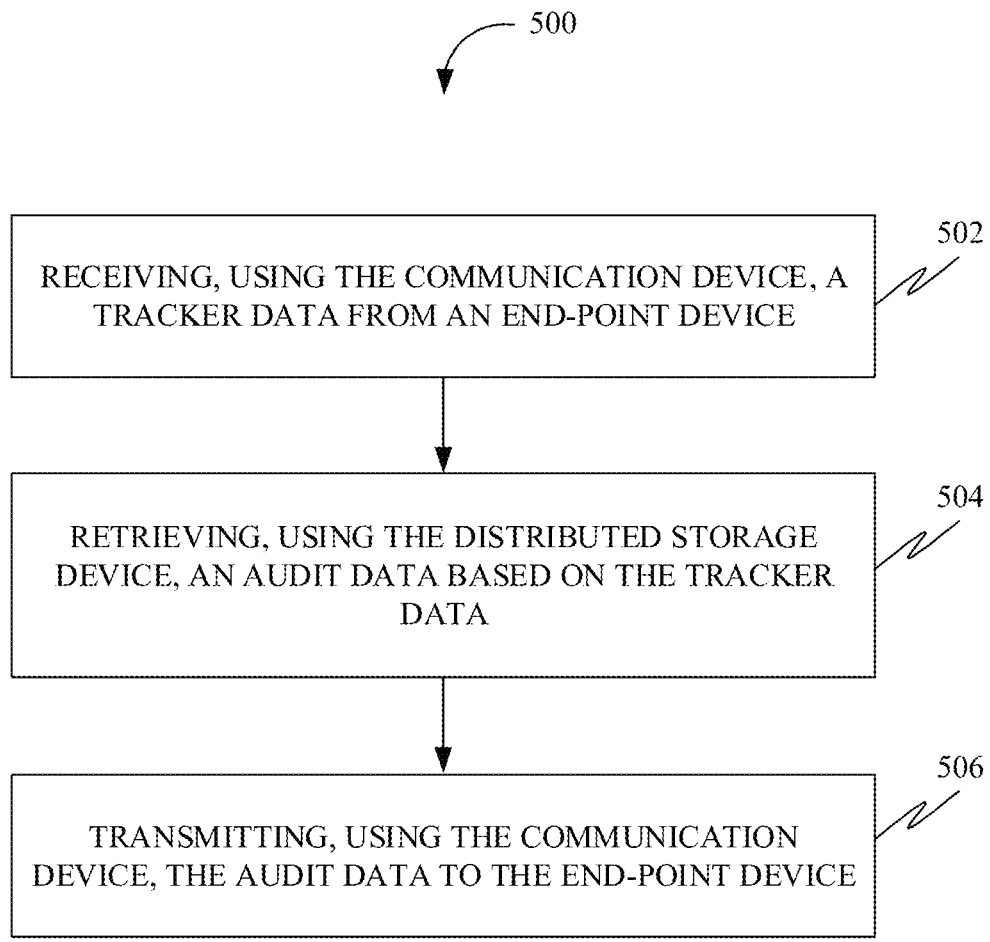
FIG. 5 is a flowchart of a method of transmitting an audit data to an end-point device, in accordance with some embodiments.

Further, at 408, the method 400 may include generating, using the processing device, the audit data based on the location data, the user identifier data and the time data. FIG. 5 is a flowchart of a method 500 of transmitting an audit data to an end-point device, in accordance with some embodiments. Further, at 502, the method 500 may include receiving, using the communication device, a tracker data from an end-point device.

Further, at 504, the method 500 include retrieving, using the distributed storage device, an audit data based on the tracker data.

Further, at 506, the method 500 include transmitting, using the communication device, the audit data to the end-point device.

Figure 6:
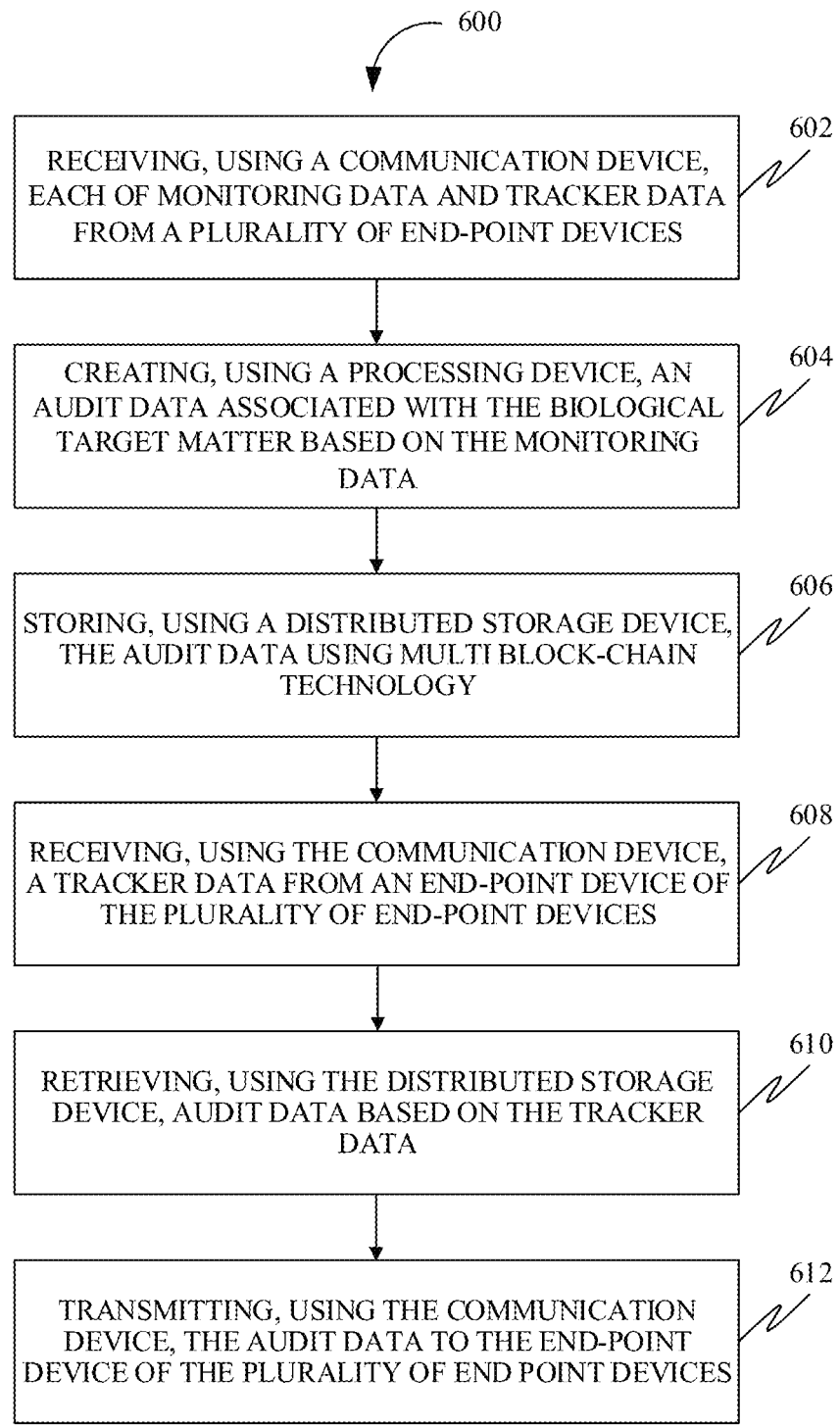
FIG. 6 is a flowchart of a method to facilitate audit data to end-point devices, in accordance with some embodiments.

FIG. 6 is a flowchart of a method 600 to facilitate audit data to end-point devices, in accordance with some embodiments. Further, at 602, the method 600 may include receiving, using a communication device, each of monitoring data and tracker data from a plurality of end-point devices. Further, each of the plurality of end-point devices may include a communication device configured to communicate over a communication network such as, but not limited to, a cellular network, a satellite network, a personal area network, Bluetooth, Internet and so on. Further various types of sensors may be embedded on the biological target matter. For an instance, the sensors may include, but may not be limited to RFID, NFC, nano-transmitters, other types of sensors etc. The sensors may provide the monitoring data as well as the tracker data.

Further, at 604, the method 600 may include creating, using a processing device, an audit data associated with the biological target matter based on the monitoring data. The biological target matter may include a medicinal herb such as cannabis. Further, audit data may include a data file in which data about the biological target matter such as plant type, genome sequencing, batch number etc. may be registered.

Further, at 606, the method 600 may include storing, using a distributed storage device, the audit data using multi block-chain technology. The block-chain technology may provide a secure way to store data and may ensure that the data may not get tempered and lost.

Further, at 608, the method 600 may include receiving, using the communication device, a tracker data from an end-point device of the plurality of end point devices. For an instance, a user may scan a particular batch of the target matter to obtain the audit data from scanning device such as a QR scanner, a barcode scanner etc.

Further, at 610, the method 600 may include retrieving, using the distributed storage device, audit data based on the tracker data.

Further, at 612, the method 600 may include transmitting, using the communication device, the audit data to the end-point device of the plurality of end point devices.

Figure 7:
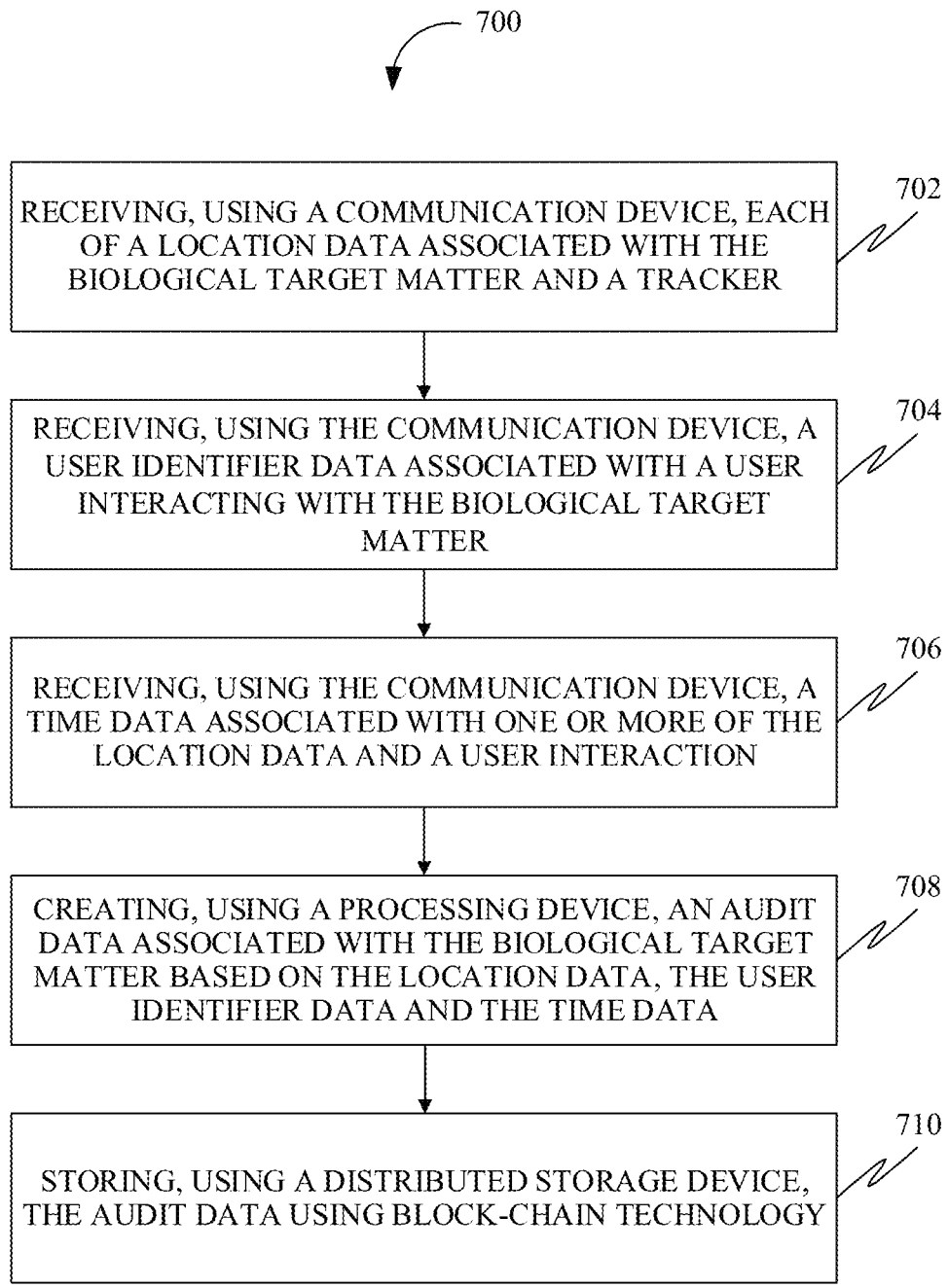
FIG. 7 is a flowchart of a method to facilitate provisioning of auditable data of the biological target matter while tracking the biological target matter, in accordance with some embodiments.

FIG. 7 is a flowchart of a method 700 to facilitate provisioning of auditable data of the biological target matter while tracking the biological target matter, in accordance with some embodiments. Further, at 702, the method 700 may include receiving, using a communication device, each of a location data associated with the biological target matter and a tracker. For an instance, the location data may be provided by a GPS device that may be embedded within a container in which the biological target matter may be transported.

Further, at 704, the method 700 may include receiving, using the communication device, a user identifier data associated with a user interacting with the biological target matter. Further, the user identifier data may be data that may help to identify the identity of the user such as name, age, medical history etc. For an instance, if the driver of the vehicle in which the biological target matter is being transported is replaced by another driver then the user identifier data associated with the new driver would be received.

Further, at 706, the method 700 may include receiving, using the communication device, a time data associated with one or more of the location data and a user interaction. The time data in combination with user identifier data as well as location data may provide secure transportation of the biological target matter.

Further, at 708, the method 700 may include creating, using a processing device, an audit data associated with the biological target matter based on the location data, the user identifier data and the time data.

Further, at 710, the method 700 may include storing, using a distributed storage device, the audit data using block-chain technology. The block-chain technology may provide a secure way to store data and may ensure that the data may not get tempered and lost.

Figure 8:
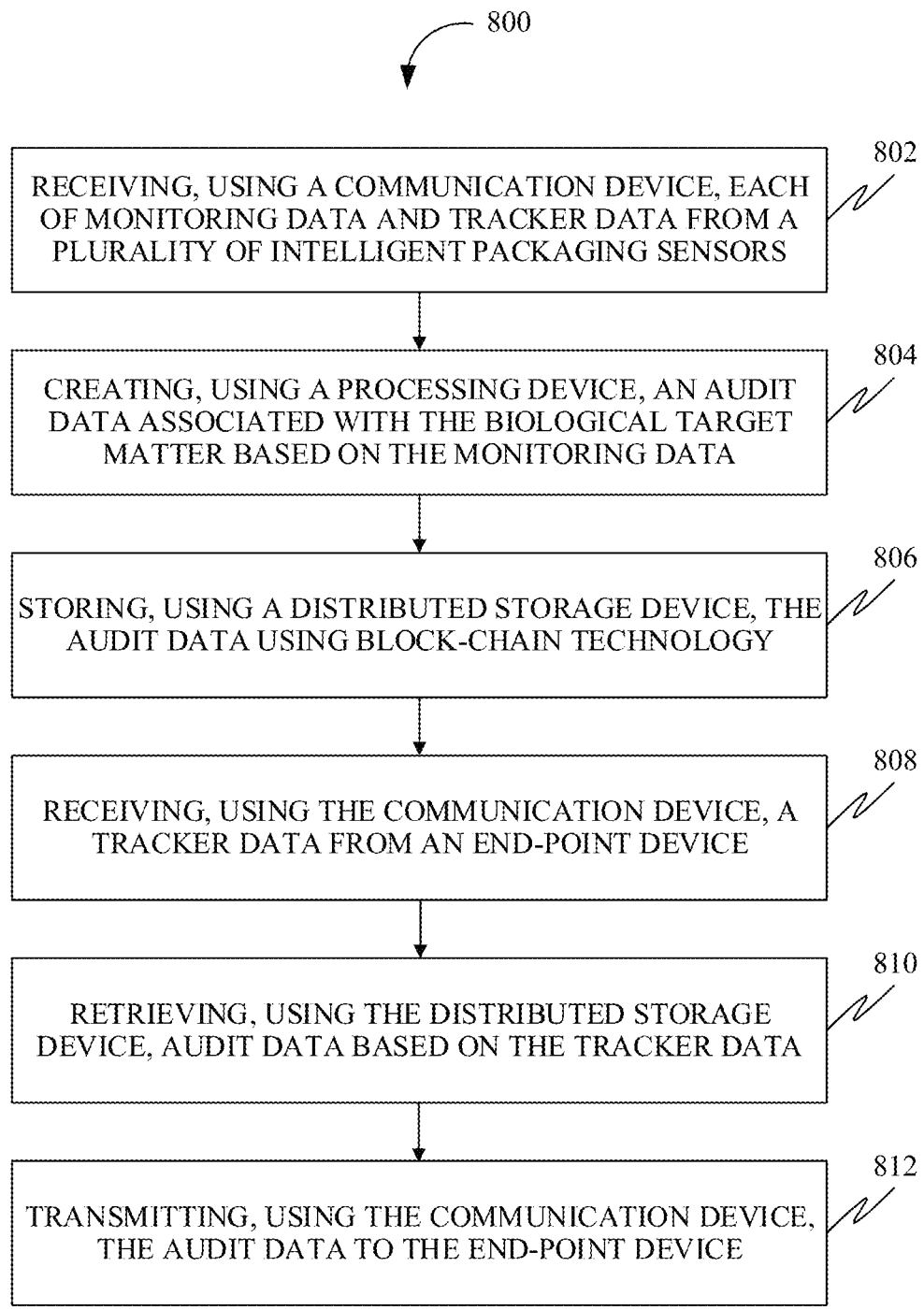
FIG. 8 is a flowchart of a method to facilitate provisioning of auditable data of the biological target matter present inside smart packages, in accordance with some embodiments.

FIG. 8 is a flowchart of a method 800 to facilitate provisioning of auditable data of the biological target matter present inside smart packages, in accordance with some embodiments.

Further, at 802, the method 800 may include receiving, using a communication device, each of monitoring data and tracker data from a plurality of intelligent packaging sensors. The plurality of intelligent packaging sensors may be installed on the smart packages of the biological target matter. The smart packages may be embedded with IoT tags that may communicate with the intelligent packaging sensors. The smart packages may contain a biometric sensor. Further, the intelligent packaging sensors such as nano-sensors may receive monitoring as well as tracker data from the biological target matter. Accordingly, the intelligent packaging sensors may transmit monitoring as well as tracker data.

Further, at 804, the method 800 may include creating, using a processing device, an audit data associated with the biological target matter based on the monitoring data. For instance, the monitoring data may include elemental data associated with the biological target matter; such as in use case of legal cannabis THC, THCA, CBD, CBN etc.

Further, at 806, the method 800 may include storing, using a distributed storage device, the audit data using block-chain technology. The block-chain technology may provide a secure way to store data and may ensure that the data may not get tempered and lost.

Further, at 808, the method 800 may include receiving, using the communication device, a tracker data from an end-point device. For example, the endpoint device such as a scanner may scan the biological target matter and may transmit the tracker data through the communication device.

Further, at 810, the method 800 may include retrieving, using the distributed storage device, audit data based on the tracker data.

Further, at 812, the method 800 may include transmitting, using the communication device, the audit data to the end-point device.

Figure 9:
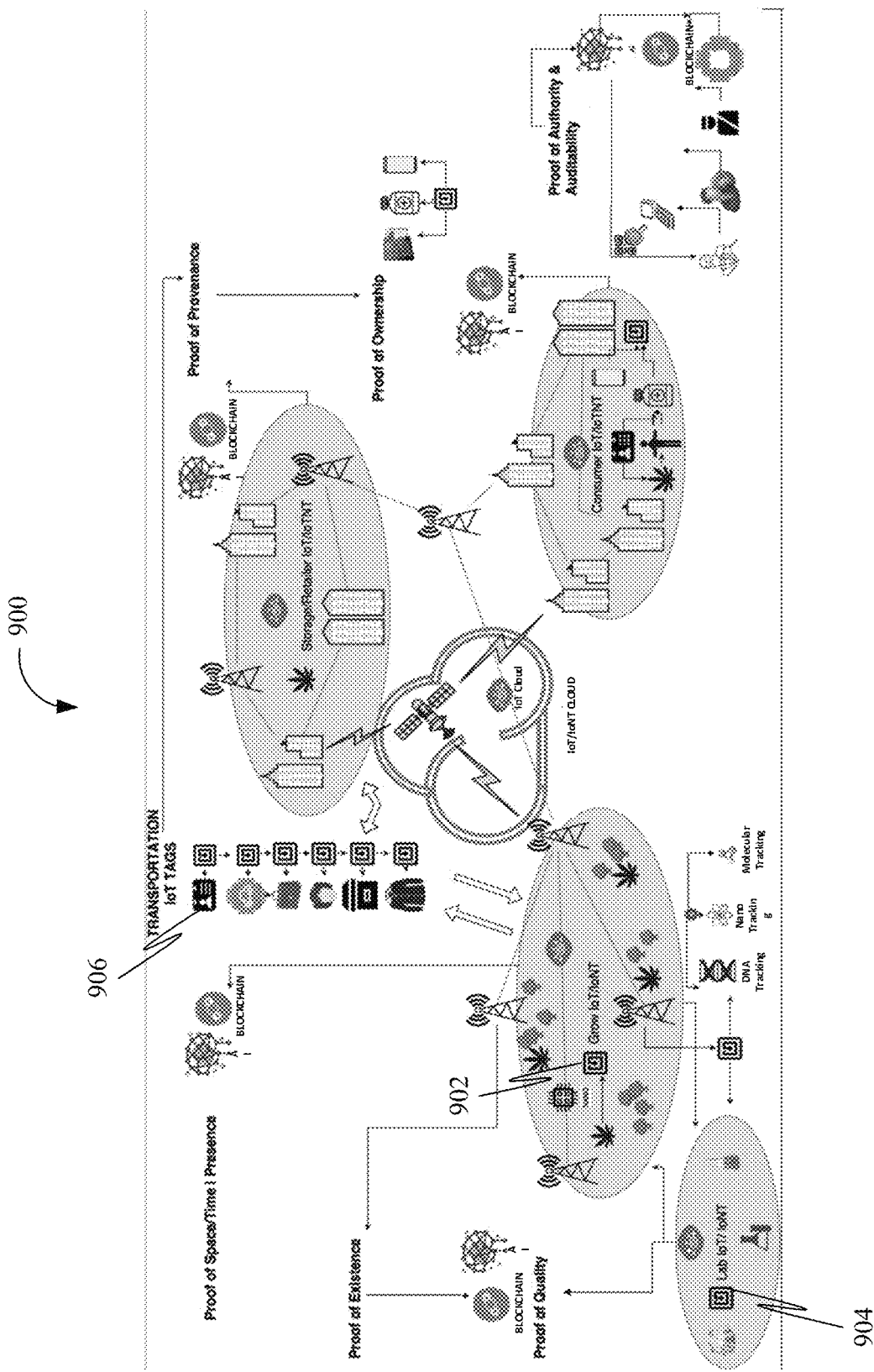
FIG. 9 is an exemplary representation of a system to facilitate provisioning of an audit data corresponding to a biological target matter, in accordance with some embodiments.
Figure 10:
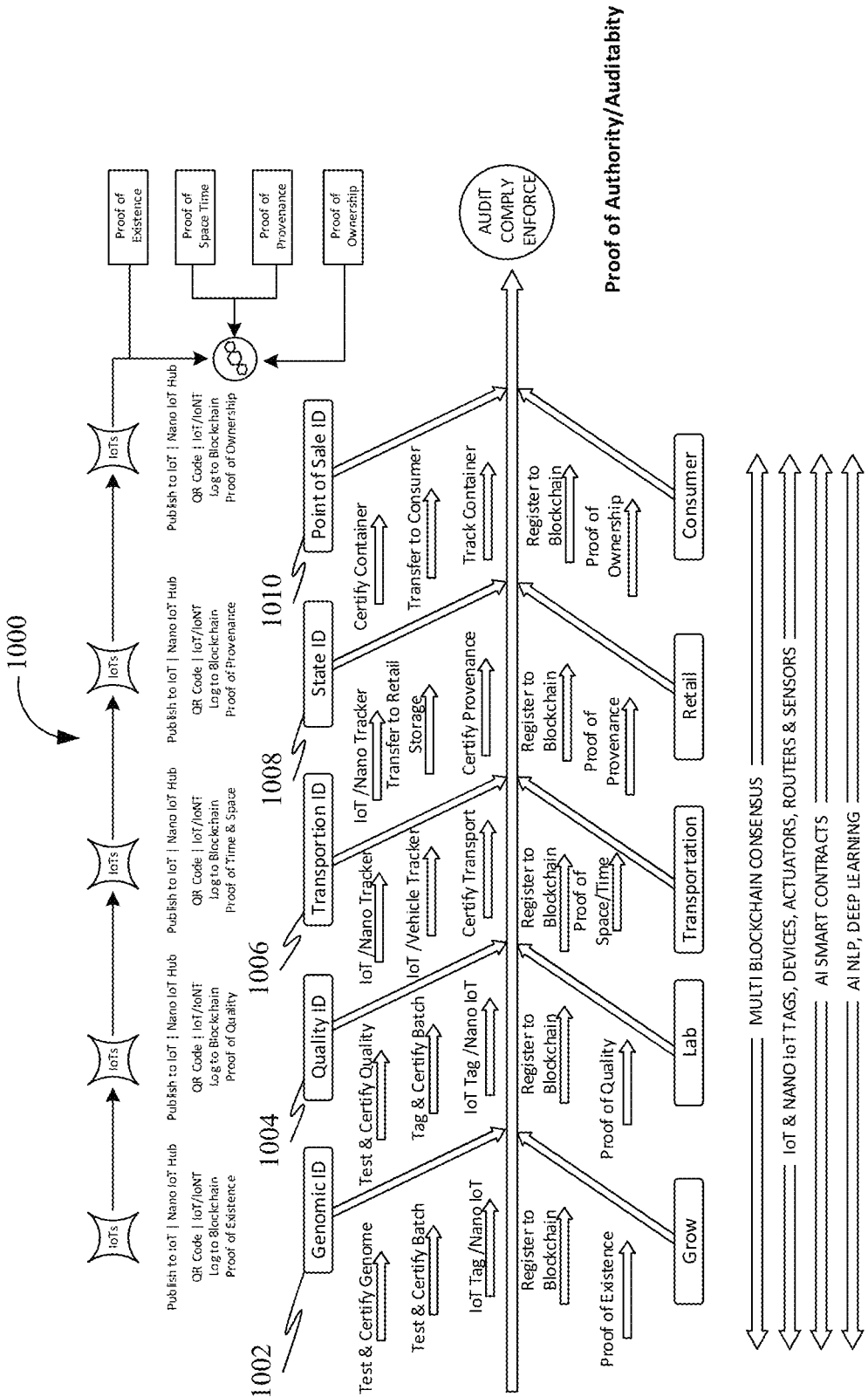
FIG. 10 is an exemplary flowchart of a method to facilitate provisioning of an audit data corresponding to a biological target matter, in accordance with some embodiments.

FIG. 9 is an exemplary representation of a system 900 to facilitate provisioning of an audit data corresponding to a biological target matter, in accordance with some embodiments. Further, FIG. 10 is an exemplary flowchart of a method 1000 to facilitate provisioning of an audit data corresponding to a biological target matter. Further, one or more steps of the method 1000 may be performed by the system 900.

Further, at 1002, method 1000 may include growing a biological target matter, such as cannabis, and receiving, using a communication device, genomic data such as genome sequencing, property and elemental data such as percentages of THC, CBD, and CBN etc. such as through testing of the biological target matter such as cannabis. Further, the method 1000 may include generating a genomic id based on the genomic data and the test results certifying the genetic structure of the biological target matter through a computing device such as a distributed computer. Further, the method 1000 may include storing a proof of existence of the biological target matter through an AI Enabled Smart Contract, including IoT tagging and tracking, and IoNT nano-marking and tracking of an IoT device 902, sensorial scanning, and phyto-tracking. Further, the proof of existence may be stored to a block-chain Further, at 1004, the method 1000 may include testing of the biological target matter in a laboratory. Further, a quality id may be generated based on elemental data through a computing device 904, such as a distributed computer. The quality id may certify the quality of the biological target matter. Further, a proof of quality of the biological target matter may be stored on a block-chain through an AI enabled smart contract including batch IoT tagging, genomic ID, batch ID, state ID, IoT tracking, IoT nano-marking and tracking.

Further, at 1006, the method may include receiving, each of a location data associated with the biological target matter and a tracker during transportation. For instance, the location data may be provided by a GPS device that may be embedded within a container in which the biological target matter may be transported.

Further, a transportation id may be generated. The transportation id may be generated to help identify a transporter of the biological target matter. The transportation id may contain the name, age, biometric information of the transporter. For an instance, if a driver of a vehicle in which the biological target matter is being transported is replaced by another driver then the user identifier data associated with the new driver would be received. Further, a time data associated with one or more of the location data and a user interaction may be received. The time data in combination with transportation id may provide secure transportation of the biological target matter. Further, a proof of space/time of the biological target matter may be stored on the block-chain through an AI enabled smart contract that may certify a carrier and approve transport through IoT tagging and tracking on vehicle (self-driving or v2v), IoT tags and tracking on clothes 906, and or accessories of authorized carrier, IoT tagging and tracking on id of authorized carrier, IoT tagging and tracking on transport container, IoT nano-tracking, and visual scanning and face recognition of carrier.

Further, at 1008, the method 1000 may include retail of the biological target matter to a user. Further, a state id of the biological target matter may be generated. The state id may include customer details such as name, age, type of usage etc. Further, the state id may be stored on one or more IoT chips and the block-chain. For instance, an enforcer may scan an IoT tag of the biological target matter in order to know the provenance of the biological target matter. Further, a proof of provenance of biological target matter may be stored on the block-chain through an AI enabled smart contract along with an IoT id and tagged id, and IoT storage tagged container.

Further, at 1010 the method 1000 may include receiving user identifier data associated with the user interacting with the biological target matter. The user identifier data may help to identify the user such as name, age, medical card id, recreational card id etc. Further, a proof of ownership may be stored on the block-chain through an AI enabled smart contract including an IoT ID, IoT consumer container ID, and an ID of a Point of Sale device used to make the retail to the consumer.

Further, an auditable data associated with the biological target matter based on the location data, the transportation id, and the time data may be generated. Further, the audit data may be stored on the block-chain. In some embodiments, the audit data may be stored on an IoT tag and may be read by an NFC enabled device such as a mobile phone. Further, a proof of authority & auditability may be stored on the block-chain through an AI enabled smart contract including an IoT/IoNT block-chain audit trail to verify ownership, verify existence, verify provenance, verify space/time-presence, and scan nano-tracker using a nano-test kit Further, a tracker data from an endpoint device may be received. For instance, the user may scan a particular batch of the biological target matter using a scanning device such as a QR scanner, a barcode scanner to obtain the audit data.

Further, the audit data based on the tracker data may be retrieved from the block-chain. Finally, the audit data may be transmitted to the end-point devices.

Figure 11:
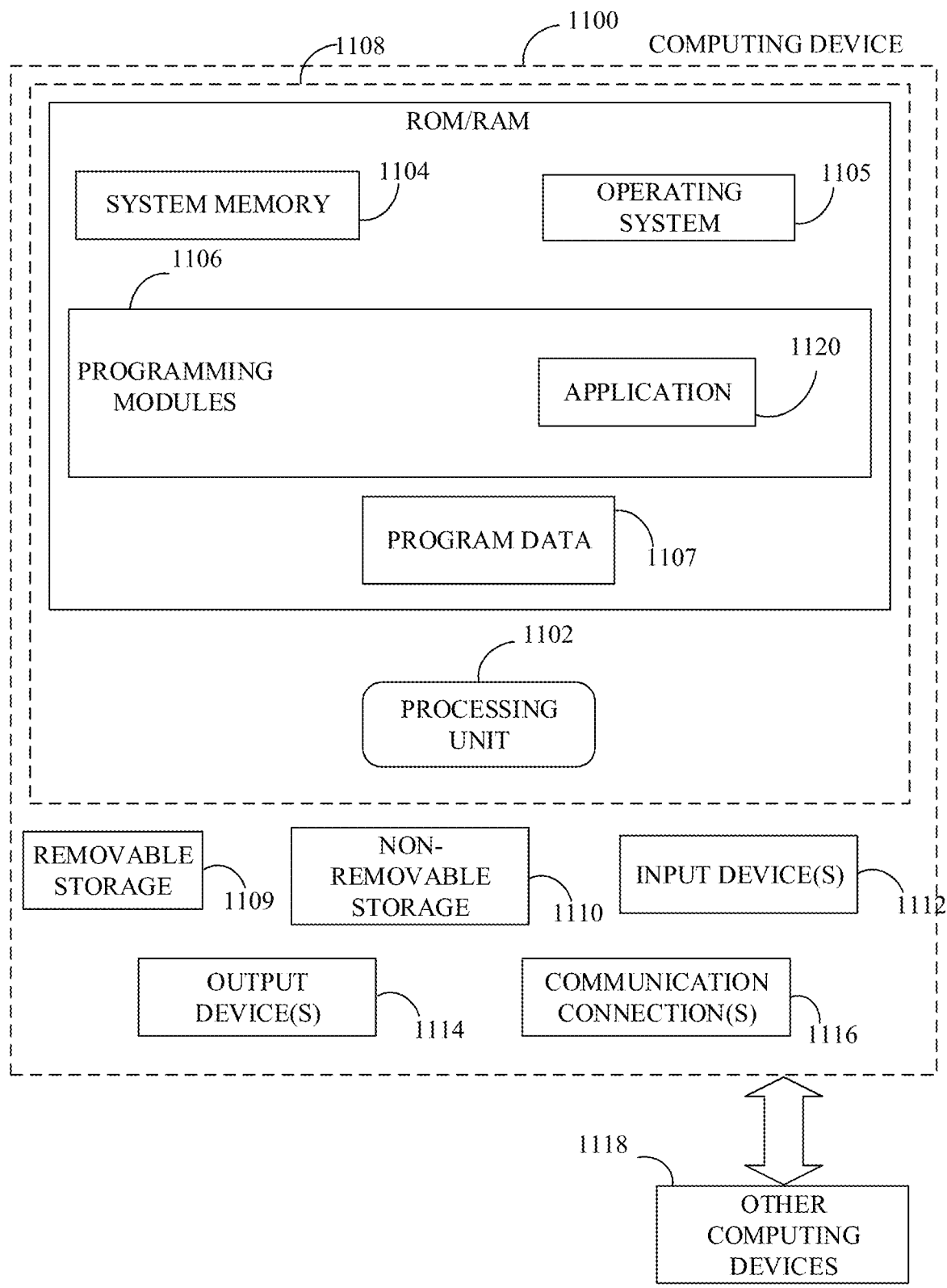
FIG. 11 is a block diagram of a computing device for implementing the methods disclosed herein, in accordance with some embodiments.

With reference to FIG. 11, a system consistent with an embodiment of the disclosure may include a computing device or cloud service, such as computing device 1100. In a basic configuration, computing device 1100 may include at least one processing unit 1102 and a system memory 1104. Depending on the configuration and type of computing device, system memory 1104 may comprise, but is not limited to, volatile (e.g. random-access memory (RAM)), non-volatile (e.g. read-only memory (ROM)), flash memory, or any combination. System memory 1104 may include operating system 1105, one or more programming modules 1106, and may include a program data 1107. Operating system 1105, for example, may be suitable for controlling computing device 1100's operation. In one embodiment, programming modules 1106 may include image-processing module, machine learning module. Furthermore, embodiments of the disclosure may be practiced in conjunction with a graphics library, other operating systems, or any other application program and is not limited to any particular application or system. This basic configuration is illustrated in FIG. 11 by those components within a dashed line 1108.

Computing device 1100 may have additional features or functionality. For example, computing device 1100 may also include additional data storage devices (removable and/or non-removable) such as, for example, magnetic disks, optical disks, or tape. Such additional storage is illustrated in FIG. 11 by a removable storage 1109 and a non-removable storage 1110. Computer storage media may include volatile and non-volatile, removable and non-removable media implemented in any method or technology for storage of information, such as computer-readable instructions, data structures, program modules, or other data. System memory 1104, removable storage 1109, and non-removable storage 1110 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1100. Any such computer storage media may be part of device 1100. Computing device 1100 may also have input device(s) 1112 such as a keyboard, a mouse, a pen, a sound input device, a touch input device, a location sensor, a camera, a biometric sensor, etc. Output device(s) 1114 such as a display, speakers, a printer, etc. may also be included. The aforementioned devices are examples and others may be used.

Computing device 1100 may also contain a communication connection 1116 that may allow device 1100 to communicate with other computing devices 1118, such as over a network in a distributed computing environment, for example, an intranet or the Internet. Communication connection 1116 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 1104, including operating system 1105. While executing on processing unit 1102, programming modules 1106 (e.g., application 1120 such as a media player) may perform processes including, for example, one or more stages of methods, algorithms, systems, applications, servers, databases as described above. The aforementioned process is an example, and processing unit 1102 may perform other processes. Other programming modules that may be used in accordance with embodiments of the present disclosure may include machine learning applications.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

What is claimed is:

1. A method to facilitate provisioning of an audit data corresponding to a biological target matter, the method comprising:
   receiving, using a communication device, a monitoring data and a tracker data associated with the biological target matter from at least one of a plurality of endpoint devices;
   creating, using a processing device, the audit data associated with the biological target matter based on at least one of the monitoring data and the tracker data;
   storing, using a distributed storage device, the audit data using block-chain technology;
   wherein the tracker data comprises a value of a biological parameter associated with the biological target matter, and sensor data received from a packaging sensor associated with the packaging of the biological target matter;
   wherein the packaging sensor comprises a nano-transmitter; and
   wherein the processing device is further configured to use artificial intelligence to perform detect changes in the genomic structure of a monitored plant.

2. The method of claim 1, wherein the creating the audit data further comprising:
   receiving, using the communication device, a location data associated with the biological target matter;

receiving, using the communication device, a user identifier data associated with a user interacting with the biological target matter;

receiving, using the communication device, a time data associated with one or more of the location data and the user interaction; and generating, using the processing device, the audit data based on the location data, the user identifier data and the time data.

3. The method of claim 1, wherein the monitoring data comprises at least one of a location data of the biological target matter, a user interaction data, and a time data associated with a user interaction.

4. The method of claim 3, wherein the monitoring data comprises chemical composition of the biological target matter.

5. The method of claim 1, wherein the packaging sensor comprises an RFID tag, an NFC chip, and an Internet of Things (IoT) tag.

6. The method of claim 1, wherein the audit data is stored on an IoT tag associated with the biological target matter.

7. The method of claim 1, wherein the processing device is further configured to use artificial intelligence to perform:
monitor at least one of a soil or a water during the growing phase of a plant, wherein the biological target matter is obtained from the plant;
track the biological target matter during transportation and distribution;
generating smart contracts; and
providing analytics data related to the growing, transportation, and distribution of the biological parameter.

8. The method of claim 7, wherein the processing device is further configured to use Natural Language Processing (NLP) to generate smart contracts based on voice commands of a user.

9. The method of claim 1 further comprising:
receiving, using the communication device, a tracker data from an end-point device;
retrieving, using the distributed storage device, an audit data based on the tracker data; and
transmitting, using the communication device, the audit data to the end-point device.

10. A system to facilitate provisioning of an audit data corresponding to a biological target matter, the system comprising:
a communication device configured for receiving a monitoring data and a tracker data associated with the biological target matter from at least one of a plurality of end-point devices;
a processing device configured for creating the audit data associated with the biological target matter based on at least one of the monitoring data and the tracker data;
a distributed storage device configured for storing the audit data using block-chain technology;

wherein the tracker data comprises a value of a biological parameter associated with the biological target matter, and sensor data received from a packaging sensor associated with the packaging of the biological target matter;

wherein the packaging sensor comprises a nano-transmitter; and wherein the processing device is further configured to use artificial intelligence to perform detect changes in the genomic structure of a monitored plant.

11. The system of claim 10, wherein,
the communication device is further configured for:
receiving, a location data associated with the biological target matter;
receiving, a user identifier data associated with a user interacting with the biological target matter; and
receiving a time data associated with one or more of the location data and the user interaction; and
the processing device is further configured for generating the audit data based on the location data, the user identifier data and the time data.

12. The system of claim 10, wherein the monitoring data comprises at least one of a location data of the biological target matter, a user interaction data, and a time data associated with a user interaction.

13. The system of claim 12, wherein the monitoring data comprises chemical composition of the biological target matter.

14. The system of claim 10, wherein the packaging sensor comprises an RFID tag, an NFC chip, and an Internet of Things (IoT) tag.

15. The system of claim 10, wherein the audit data is stored on an IoT tag associated with the biological target matter.

16. The system of claim 10, wherein the processing device is further configured to use artificial intelligence to perform:
monitor at least one of a soil or a water during the growing phase of a plant, wherein the biological target matter is obtained from the plant;
track the biological target matter during transportation and distribution;
generating smart contracts; and
providing analytics data related to the growing, transportation, and distribution of the biological parameter.

17. The system of claim 16, wherein the processing device is further configured to use Natural Language Processing (NLP) to generate smart contracts based on voice commands of a user.

18. The system of claim 10, wherein
the communication device is further configured for:
receiving a tracker data from an end-point device; and
transmitting, an audit data to the end-point device; and
the distributed storage device is further configured for retrieving the audit data based on the tracker data.

* * * * *